United States Patent
Jo et al.

(10) Patent No.: US 10,524,659 B2
(45) Date of Patent: Jan. 7, 2020

(54) ELECTRONIC APPARATUS, METHOD FOR CONTROLLING THE SAME, AND COMPUTER-READABLE RECORDING MEDIUM

(71) Applicant: Samsung Electronics Co., Ltd., Gyeonggi-do (KR)

(72) Inventors: Seong-wook Jo, Gyeonggi-do (KR); Su-ho Lee, Gyeonggi-do (KR); Jin-seob Kim, Gyeonggi-do (KR); Jae-hyun Park, Seoul (KR); Yong-chan Lee, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 15/378,828

(22) Filed: Dec. 14, 2016

(65) Prior Publication Data
US 2017/0164833 A1 Jun. 15, 2017

(30) Foreign Application Priority Data

Dec. 15, 2015 (KR) .......................... 10-2015-0179323

(51) Int. Cl.
*A61B 5/00* (2006.01)
*A61B 5/0402* (2006.01)
(Continued)

(52) U.S. Cl.
CPC .......... *A61B 5/0002* (2013.01); *A61B 5/0022* (2013.01); *A61B 5/02055* (2013.01);
(Continued)

(58) Field of Classification Search
CPC . A61B 5/0002; A61B 5/0022; A61B 5/02055; A61B 5/746; A61B 5/74;
(Continued)

(56) References Cited

U.S. PATENT DOCUMENTS

2001/0037070 A1* 11/2001 Cranley ................. A61B 5/00 600/532
2008/0208015 A1* 8/2008 Morris ................... A61B 5/165 600/301

(Continued)

FOREIGN PATENT DOCUMENTS

JP 2003275180 9/2003
JP 2008-252852 10/2008
(Continued)

OTHER PUBLICATIONS

International Search Report dated Feb. 20, 2017 issued in counterpart applicaton No. PCT/KR2016/013862, 8 pages.
(Continued)

*Primary Examiner* — Minjung Kim
(74) *Attorney, Agent, or Firm* — The Farrell Law Firm, P.C.

(57) ABSTRACT

An electronic apparatus is provided. The electronic apparatus includes a communicator configured to receive a plurality of biometric (bio) signals of a user from an external device; and a processor configured to determine a body condition of the user according to whether each of the received plurality of bio signals is in a normal range, wherein the processor, is further configured to control the communicator to transmit information about the determined body condition to an external device corresponding to the determined body condition among a plurality of external devices, and wherein the determination of a body condition varies as a function of the user having either a symptom or a disease.

15 Claims, 12 Drawing Sheets

(51) Int. Cl.
*A61B 5/024* (2006.01)
*A61B 5/0205* (2006.01)
*A61B 5/021* (2006.01)
*G16H 40/67* (2018.01)

(52) U.S. Cl.
CPC ............... *A61B 5/74* (2013.01); *A61B 5/742* (2013.01); *A61B 5/746* (2013.01); *G16H 40/67* (2018.01); *A61B 5/021* (2013.01); *A61B 5/024* (2013.01); *A61B 5/0402* (2013.01); *A61B 5/741* (2013.01)

(58) Field of Classification Search
CPC ....... A61B 5/742; A61B 5/0402; A61B 5/021; A61B 5/024
See application file for complete search history.

(56) References Cited

U.S. PATENT DOCUMENTS

| | | | |
|---|---|---|---|
| 2008/0228349 A1* | 9/2008 | Nakamura | B60R 21/01538 701/33.4 |
| 2012/0157790 A1 | 6/2012 | Park et al. | |
| 2013/0072765 A1* | 3/2013 | Kahn | A61B 5/01 600/301 |
| 2013/0131465 A1* | 5/2013 | Yamamoto | A61B 5/7271 600/301 |
| 2013/0278414 A1* | 10/2013 | Sprigg | G08B 21/0453 340/539.12 |
| 2015/0019131 A1* | 1/2015 | Basir | G01C 21/26 701/526 |
| 2015/0052618 A1* | 2/2015 | Michalske | G06F 21/31 726/27 |
| 2015/0195696 A1 | 7/2015 | Shukla et al. | |

FOREIGN PATENT DOCUMENTS

| | | |
|---|---|---|
| JP | 2012256281 | 12/2012 |
| KR | 1020090107414 | 10/2009 |
| KR | 201200134496 | 7/2012 |
| KR | 20120138313 | 12/2012 |
| KR | 101427747 | 8/2014 |
| KR | 1020150061195 | 6/2015 |
| KR | 1020150061745 | 6/2015 |

OTHER PUBLICATIONS

S. Noh et al., "Ferroelectret Film-Based Patch-Type Sensor for Continuous Blood Pressure Monitoring", Electronic Letters, Jan. 30, 2014, 2 pages.

Xavier Jouven et al., "Heart-Rate Profile During Exercise as a Predictor of Sudden Death", The New England Journal of Medicine, May 12, 2005, 8 pages.

* cited by examiner

ELECTRONIC APPARATUS, METHOD FOR CONTROLLING THE SAME, AND COMPUTER-READABLE RECORDING MEDIUM

PRIORITY

This application claims priority under 35 U.S.C. § 119(a) to a Korean Patent Application filed on Dec. 15, 2015 in the Korean Intellectual Property Office and assigned Serial No. 10-2015-0179323, the entire contents of which are incorporated herein by reference.

BACKGROUND

1. Field of the Disclosure

The present disclosure relates generally to an electronic apparatus, a method for controlling the same, and a non-transitory computer-readable recording medium, and more particularly, to an electronic apparatus that performs healthcare of a user in stages according to a body state of the user, a method for controlling the same, and a non-transitory computer-readable recording medium.

2. Description of the Related Art

The human life span has been greatly increased due to developments in medical technology. Accordingly, the number of people requiring continuous healthcare such as the elderly, the chronically ill, the obese, and adult disease patients, etc. have greatly increased. In particular, recently, the number of people with chronic diseases such as hypertension or diabetes have greatly increased.

These people need continuous health care in their daily life. It is common that even though they are in a dangerous state or have developed complications, since they have no subjective symptom, they neglect their health care, which makes their conditions worse.

As the number of one person households increases, if the elderly or the chronically ill are alone and an emergency occurs, a quick rescue may not be made, which often makes a patient's condition worse.

Therefore, there is a need for a technology for frequently checking a body condition of a patient in daily life in order to prevent the patient's condition from getting worse in the absence of recognition of a worsening condition by the patient and providing a quick rescue response within an opportune or golden time so as to save the life of the patient if the patient experiences an emergency.

SUMMARY

An aspect of the present disclosure provides an electronic apparatus capable of frequently checking a body condition of a user to provide health care to the user in stages, and provide a quick rescue response if the user experiences an emergency, a method for controlling the same, and a non-transitory computer-readable recording medium.

Another aspect of the present disclosure provides a processor that may determine a body condition as one of a normal condition, a caution condition, a danger condition, and an emergency condition based on a received plurality of biometric or bio signals.

Another aspect of the present disclosure provides a processor that may transmit information about a body condition to a first external device carried by a user if a determined body condition is a caution condition, transmit the information about the body condition to at least one second external device designated by the user if the determined body condition is a danger condition, and transmit the information about the body condition to a third external device arranged in a public center if the determined body condition is an emergency condition.

Another aspect of the present disclosure provides an electronic apparatus that may include a display configured to display information about a determined body condition.

Another aspect of the present disclosure provides a processor that may control a communicator to transmit a notification to an emergency center if a determined body condition is an emergency condition and the emergency condition continues for more than a preset time.

Another aspect of the present disclosure provides an electronic apparatus that may include an imaging unit configured to generate an image; and a microphone configured to generate voice information, wherein a processor operates at least one of the imaging unit and the microphone if a determined body condition is an emergency condition and controls a communicator to transmit at least one of the image generated by the imaging unit and the voice information generated by the microphone to an external device.

Another aspect of the present disclosure provides a processor that may determine a body condition of a user in consideration of previously stored disease information of the user.

Another aspect of the present disclosure provides a processor that may determine a body condition of a user by using a first group of bio signals among a received plurality of bio signals if a preset condition is satisfied and determine the body condition of the user by further using a second group of bio signals among the received plurality of bio signals if the preset condition is not satisfied.

Another aspect of the present disclosure provides a second group of bio signals that may be received if a preset condition is not satisfied.

Another aspect of the present disclosure provides a processor that may sense a movement of an external device by using a change in a receiving direction of a wireless communication signal transmitted from an external device, and, if the movement of the external device is not sensed for a preset time, control a communicator to request the external device to transmit a plurality of bio signals of a user.

Another aspect of the present disclosure determines a body condition as one of a normal condition, a caution condition, a danger condition, and an emergency condition based on a received plurality of bio signals.

Another aspect of the present disclosure transmits information about a body condition to a first external device carried by a user if a determined body condition is a caution condition; transmit the information about the body condition to at least one second external device designated by the user if the determined body condition is a danger condition; and transmitting the information about the body condition to a third external device arranged in a public center if the determined body condition is an emergency condition.

Another aspect of the present disclosure displays information about a determined body condition.

Another aspect of the present disclosure transmits a notification to an emergency center if a determined body condition is an emergency condition and the emergency condition continues for more than a preset time.

Another aspect of the present disclosure operates at least one of an imaging unit configured to generate an image and a microphone configured to generate voice information if a determined body condition is an emergency condition; and transmits at least one of the image generated by the imaging unit and the voice information generated by the microphone to an external device.

Another aspect of the present disclosure determines a body condition of a user in consideration of previously stored disease information of the user.

Another aspect of the present disclosure determines a body condition of a user by using a first group of bio signals among a received plurality of bio signals if a preset condition is satisfied and determines the body condition of the user by further using a second group of bio signals among the received plurality of bio signals if the preset condition is not satisfied.

Another aspect of the present disclosure senses a movement of an external device by using a change in a receiving direction of a wireless communication signal transmitted from an external device; and if the movement of the external device is not sensed for a preset time, requests the external device to transmit a plurality of bio signals of a user.

According to an aspect of the present disclosure, an electronic apparatus is provided. The apparatus includes a communicator configured to receive a plurality of bio signals of a user from an external device; and a processor configured to determine a body condition of the user according to whether each of the received plurality of bio signals is in a normal range, wherein the processor is further configured to control the communicator to transmit information about the determined body condition to an external device corresponding to the determined body condition among a plurality of external devices, and wherein the determination of a body condition varies as a function of the user having either a symptom or a disease.

According to another aspect of the present disclosure, a method for controlling an electronic apparatus is provided. The method includes receiving, by a communicator, a plurality of bio signals of a user from an external device; determining, by a processor, a body condition of the user according to whether each of the received plurality of bio signals is in a normal range; and transmitting information about the determined body condition to an external device corresponding to the determined body condition among a plurality of external devices, wherein the determination of a body condition varies as a function of the user having either a symptom or a disease.

According to another aspect of the present disclosure, there is provided a non-transitory computer-readable recording medium. The non-transitory computer-readable recording medium includes a computer program for executing a method for controlling an electronic apparatus, wherein the method includes receiving a plurality of bio signals of a user from an external device; determining a body condition of the user according to whether each of the received plurality of bio signals is in a normal range; and transmitting information about the determined body condition to an external device corresponding to the determined body condition among a plurality of external devices, wherein the determination of a body condition varies as a function of the user having either a symptom or a disease.

BRIEF DESCRIPTION OF THE DRAWINGS

The above and other aspects, features, and advantages of the present disclosure will be more apparent from the following detailed description, taken in conjunction with the accompanying drawings, in which.

DETAILED DESCRIPTION OF EMBODIMENTS OF THE PRESENT DISCLOSURE

Embodiments of the present disclosure are described below in more detail with reference to the accompanying drawings. In the description of the present disclosure, certain detailed explanations of the related art are omitted when it is deemed that they may unnecessarily obscure the present disclosure. The embodiments of the present disclosure described below may, however, be embodied in many different forms and the scope of the present disclosure is not intended to be construed as being limited to the embodiments set forth herein; rather, these embodiments are provided so that the present disclosure will be thorough and complete, and will fully convey the concept of the present disclosure to those skilled in the art.

When a portion "includes" an element, another element may be further included, rather than excluding the existence of the other element, unless otherwise described. Furthermore, various elements and regions are schematically illustrated in the accompanying drawings. Thus, the present disclosure is not intended to be limited by relative sizes or gaps illustrated in the accompanying drawings.

Figure 1:
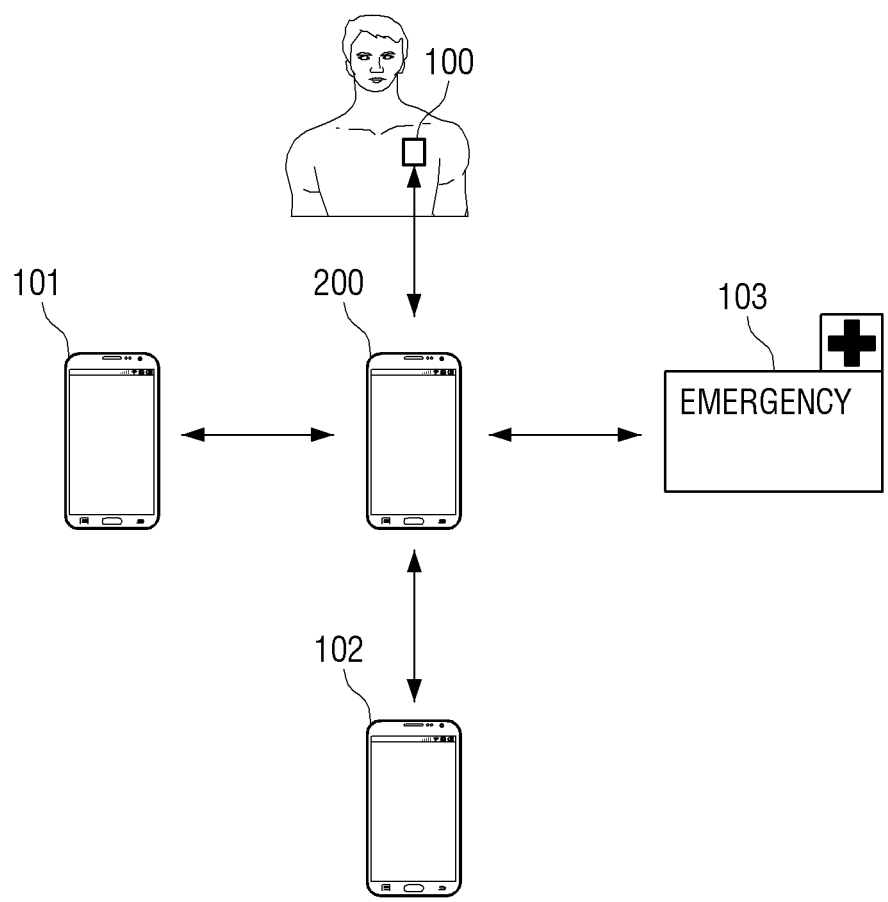
FIG. 1 illustrates a user body monitoring system using an electronic apparatus according to an embodiment of the present disclosure.

FIG. 1 illustrates a user body monitoring system 1000 using an electronic apparatus according to an embodiment of the present disclosure. For example, the electronic apparatus according to the first embodiment of the present disclosure may be a terminal apparatus 200 of a user.

Referring to FIG. 1, the user body monitoring system 1000 using the electronic apparatus according to an embodiment of the present disclosure may include an external device 100 attached to a user's body, the terminal apparatus 200 of the user, terminal apparatuses 101 and 102 of others, and an emergency center 103.

In this regard, the external device 100 attached to the user's body may measure a plurality of bio signals of the user. For example, the external device 100 may be attached to the user's body to measure the plurality of bio signals related to a basal metabolism of the user and a bio signal directly related to the life of the user. In this regard, the external device 100 may transmit the measured plurality of bio signals of the user to the terminal apparatus 200. A detailed configuration of the external device 100 is described below in greater detail with reference to FIG. 2.

In this regard, the external device 100 attached to the user's body may be a patch type device that measures a plurality of bio signals of the user. For example, the external device 100 may be a patch type device including a sensor for measuring a plurality of bio signals of the user.

Although the external device 100 attached to the user's body is limited, illustrated, and described as a patch type device for convenience of description, the external device 100 may be a band type device wearable on a part of the user's body without adhesion when practically implemented.

Although the external device 100 is described as one external device for convenience of description, a plurality of external devices may be used to measure bio signals of a user when practically implemented.

The terminal apparatus 200 of the user may receive the measured plurality of bio signals of the user from the external device 100. In this regard, the terminal apparatus 200 of the user may be used to determine the received plurality of bio signals to determine a body condition of the user. For example, the terminal apparatus 200 of the user may determine the body condition of the user as a normal condition and a condition beyond the normal condition based on the received plurality of bio signals. In this regard, the condition beyond the normal condition may be determined as one of a caution condition, a danger condition, and an emergency condition.

The terminal apparatus 200 of the user may transmit information about the body condition of the user to an external apparatus corresponding to the determined body condition of the user among the plurality of external apparatuses, for example the terminal apparatuses 101 and 102 and the emergency center 103. For example, if the terminal apparatus 200 of the user determines the body condition of the user as the normal condition, the terminal apparatus 200 of the user may continue to determine the body condition of the user based on the received bio signal of the user without a separate operation. In this regard, the terminal apparatus 200 of the user may display the body condition of the user on a display provided in the terminal apparatus 200 of the user for continuous healthcare of the user.

If the terminal apparatus 200 of the user determines the body condition of the user as the caution condition, the terminal apparatus 200 of the user may display the information about the body condition of the user on the display provided in the terminal apparatus 200 of the user to notify the user that the body condition of the user is the condition beyond the normal condition.

If the terminal apparatus 200 of the user determines the body condition of the user as the danger condition, the terminal apparatus 200 of the user may transmit the information about the body condition of the user to the at least one external apparatuses, for example the terminal apparatuses 101 and 102, designated by the user. For example, if the terminal apparatus 200 of the user determines the body condition of the user as the danger condition, the terminal apparatus 200 of the user may transmit the information about the body condition of the user to the terminal apparatuses 101 and 102 of family members of the user.

If the terminal apparatus 200 of the user determines the body condition of the user as the emergency condition, the terminal apparatus 200 of the user may transmit the information about the body condition of the user to the external apparatus 103 arranged in a public center and may request a rescue. For example, if the terminal apparatus 200 of the user determines the body condition of the user as the emergency condition, the terminal apparatus 200 of the user may transmit the information about the body condition of the user to the server 103 of the emergency center and may request a rescue. The detailed configuration of the terminal apparatus 200 of the user is described below with reference to FIG. 4 that illustrates an electronic apparatus according to an embodiment of the present disclosure described below.

In addition, the terminal apparatus 200 of the user may provide a notification while transmitting the information about the body condition of the user to the plurality of external apparatuses 101, 102, and 103.

Although the terminal apparatus 200 of the user is limited, illustrated, and described as a cellular phone of the user for convenience of description, the terminal apparatus 200 of the user may be a display apparatus such as a smart TV, a tablet personal computer (PC), a portable multimedia player (PMP), a personal digital assistant (PDA), a smart watch, etc. when practically implemented.

Although the external device 100 that measures the bio signal of the user and the terminal apparatus 200 of the user are illustrated and described to be spaced apart from each other in FIG. 1 for convenience of description, the external device 100 and the terminal apparatus 200 of the user may be an all-in-one type when practically implemented. For example, if the terminal apparatus 200 of the user is a smart watch, a wrist band part of the smart watch in contact with the body of the user may be implemented to include the external device 100 that measures the bio signal of the user.

Although the electronic device according to an embodiment of the present disclosure is limited and described as the terminal apparatus 200 of the user that is a body monitoring target in FIG. 1, the electronic device may be a terminal apparatus of another designated by the user, a public center, etc. when practically implemented.

Figure 2:
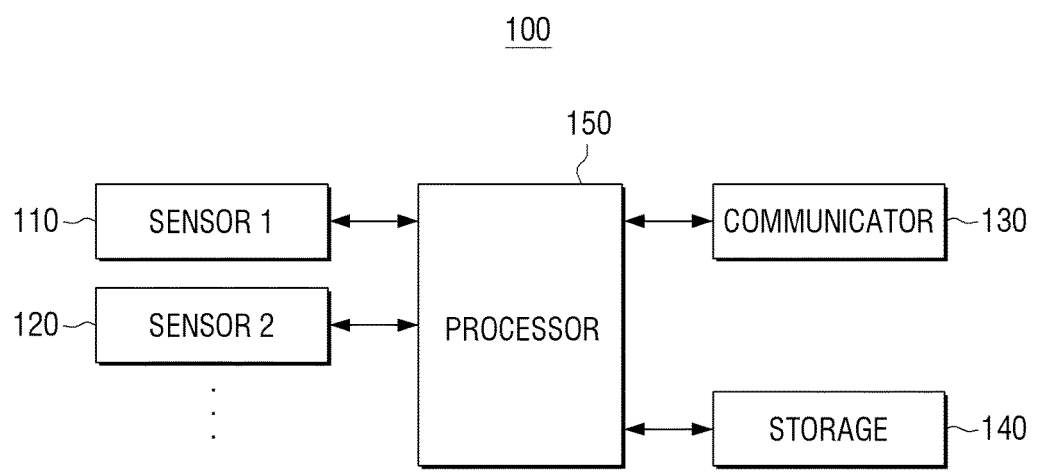
FIG. 2 is a block diagram of an external device according to an embodiment of the present disclosure.

FIG. 2 is a block diagram of the external device 100 according to an embodiment of the present disclosure.

Referring to FIG. 2, the external device 100 may include sensors 110 and 120, a communicator 130, a storage 140, and a processor 150.

In this regard, the external device 100 may be attached to a user's body to measure a plurality of bio signals of the user. For example, the external device 100 may be directly attached onto the skin of the user to measure the plurality of bio signals of the user. In this regard, the external device 100 may be a patch type device including a sensor for measuring the plurality of bio signals of the user. However, the present disclosure is not limited thereto. The external device 100 may be a band type device that is worn on a part of the body of the user and measures the plurality of bio signals of the user or may be an integrated circuit or chip type device insertable into the skin of the user.

The sensors 110 and 120 may measure the plurality of bio signals of the user. For example, the sensors 110 and 120 may be arranged in a location in contact with the skin of the user or inside the external device 100 to measure the plurality of bio signals of the user. For example, the sensors 110 and 120 may be sensors that measure at least one of blood glucose, blood pressure, cholesterol, electrocardiogram (ECG), pulse, respiration, and body temperature. Although the external device 100 includes the two sensors 110 and 120 in FIG. 2 for convenience of description, the external device 100 may include three or more sensors when practically implemented. If a plurality of external devices are used to measure the plurality of bio signals of the user, each of the plurality of external devices may include one sensor.

The communicator 130 may use not only a form connected to an external apparatus over a local area network (LAN) and the Internet but also wireless communication methods (for example, global system for mobile communications (GSM), universal mobile telecommunications system (UMTS), long term evolution (LTE), wireless broadband (WiBRO), wireless fidelity (WiFi), Bluetooth, etc.) in order to connect the external device 100 and the electronic apparatus.

For example, the communicator 130 may transmit the plurality of bio signals of the user measured by the sensors 110 and 120 to the electronic apparatus. The communicator 130 may also transmit information about the user's body determined based on the plurality of bio signals of the user measured by the sensors 110 and 120 to the electronic apparatus.

In this regard, the electronic apparatus may be at least one of a terminal apparatus of the user, a server, and an Internet sharer that transmits and receives a wireless Internet signal. The electronic apparatus according to each embodiment of the present disclosure is described below in detail with reference to FIGS. 1 and 8 through 11.

The communicator 130 may transmit and receive a wireless communication signal with the electronic apparatus. For example, the communicator 130 may transmit a wireless communication signal to the electronic apparatus to notify whether there is a movement of the external device 100. A method of determining a movement of the external device 100 using the wireless communication signal is described below in detail with reference to FIG. 10.

The communicator 130 may receive a request to measure and transmit a plurality of bio signals of a user from the electronic apparatus. For example, if the external device 100 is in a sleep mode, and if the electronic apparatus does not sense a movement of the external device 100 for a preset time, the communicator 130 may receive the request of the electronic apparatus to transmit a plurality of bio signals of the user.

In this regard, the sleep mode of the external device 100 may be a status in which it is possible to transmit and receive a wireless communication signal with a terminal apparatus or an external apparatus while the plurality of bio signals of the user are not measured in order to reduce power consumption of the external device 100.

In this regard, the external device 100 may be changed to an active mode according to a request of the electronic apparatus to measure a plurality of bio signals of the user, and the communicator 130 may transmit the measured plurality of bio signals of the user to the electronic apparatus.

The storage 140 may store a plurality of bio signals of the user measured by the sensors 110 and 120.

The processor 150 may control the sensors 110 and 120 in order to measure the plurality of bio signals of the user. For example, the processor 150 may control the sensors 110 and 120 to measure only a first group of bio signals among the plurality of bio signals if a preset condition is satisfied. The processor 150 may control the sensors 110 and 120 to further measure a second group of bio signals among the plurality of bio signals if the preset condition is not satisfied.

In this regard, the preset condition may be that preset measurement values of the first group of bio signals are all within a normal range. In this regard, if preset at least one measurement value of the first group of bio signals is beyond the normal range, the processor 150 may control the sensors 110 and 120 to further measure the second group of bio signals.

In this regard, the first group of bio signals among the plurality of bio signals may be bio signals that are related to a basal metabolism and a disease of the user and need to be continuously monitored in daily life. The second group of bio signals may be bio signals directly related to the life of the user. For example, the first group of bio signals may be at least one of blood glucose, blood pressure, ECG, pulse, and cholesterol, and the second group of bio signals may be at least one of respiration, heartbeat, and body temperature. However, this is merely an example. The plurality of bio signals may be divided into three or more groups and measured.

The processor 150 may control the communicator 130 to transmit a measured plurality of bio signals of a user to the electronic apparatus.

The processor 150 may control the communicator 130 to transmit and receive wireless communication with the electronic apparatus if the external device 100 is in a sleep mode. In this regard, the processor 150 may control the sensors 110 and 120 to change the external device 100 to an active mode and measure a plurality of bio signals if the processor 150 receives a request to transmit the plurality of bio signals of the user from the electronic apparatus through the communicator 130 and may control the communicator 130 to transmit the measured plurality of bio signals to the electronic apparatus.

The processor 150 may control the storage 140 to store a plurality of bio signals measured by the sensors 110 and 120.

The processor 150 may determine a body condition of the user by using the measured plurality of bio signals. For example, the processor 150 may determine the body condition of the user as one of a normal condition, a caution condition, a danger condition, and an emergency condition based on the measured plurality of bio signals.

In this regard, if each of the measured plurality of bio signals is within a normal range, the processor 150 may determine the body condition of the user as the normal condition. If each of the measured plurality of bio signals is beyond the normal range, the processor 150 may determine the body condition of the user as the caution condition. In this regard, the caution condition may be a condition in which a numerical value of a bio signal does not belong to the normal range but does not directly affect the life of the user.

If each of the measured plurality of bio signals is beyond the normal range and a complication symptom is sensed, the processor 150 may determine the body condition of the user as the danger condition. For example, if a diabetic having blood glucose beyond a normal range has a high blood pressure symptom, the processor 150 may determine a body condition of the diabetic as the danger condition.

If the user corresponding to the danger condition has an emergency disease, the processor 150 may determine the body condition of the user as the emergency condition. For example, if heartbeat or respiration of the diabetic having the complication symptom is beyond the normal range, the processor 150 may determine the body condition of the diabetic as the emergency condition.

The processor 150 may determine the body condition of the user in consideration of previously stored disease information of the user. For example, the processor 150 may differently apply a body condition determination standard of the user according to previously input disease information of the user. For example, with regard to blood pressure among the plurality of bio signals, if the blood pressure of the user who is in a normal person ranges from 140 millimeters of Mercury (mmHg) to 90 mmHg, the processor 150 may determine the body condition of the user as the normal condition while only if the blood pressure of the user who is a diabetic ranges from 120 mmHg to 80 mmHg, the processor 150 may determine the body condition of the user as the normal condition. That is, if the blood pressure of a diabetic is within a normal range of a normal person from 140 mmHg to 90 mmHg but is beyond the range from 120 mmHg to 80 mmHg, the processor 150 may determine the body condition of the user as the danger condition.

The processor 150 may determine the body condition of a user by using a first group of bio signals among a plurality of bio signals measured by the sensors 110 and 120 if a preset condition is satisfied. The processor 150 may determine the body condition of the user by further using a second group of bio signals among the plurality of bio signals if the preset condition is not satisfied.

In this regard, the preset condition may be that preset measurement values of the first group of bio signals are all within a normal range. If preset at least one measurement value of the first group of bio signals is beyond the normal range, the processor 150 may determine the body condition of the user by further using the second group of bio signals.

In this regard, the first group of bio signals among the plurality of bio signals may be bio signals that are related to basal metabolism and a disease of the user and need to be continuously monitored in daily life. The second group of bio signals may be bio signals directly related to the life of the user. For example, the first group of bio signals may be at least one of blood glucose, blood pressure, ECG, pulse, and cholesterol, and the second group of bio signals may be at least one of respiration, heartbeat, and body temperature. However, this is merely an example. The plurality of bio signals may be divided into three or more groups and measured when practically implemented.

The processor 150 may determine the body condition of the user by measuring only the first group of bio signals among the plurality of bio signals measured by the sensors 110 and 120 if the preset condition is satisfied, and may determine the body condition of the user by further measuring the second group of bio signals among the plurality of bio signals measured by the sensors 110 and 120 if the preset condition is not satisfied.

The processor 150 may control the communicator 130 to transmit information about the measured body condition to a corresponding external apparatus according to the determined body condition of the user among a plurality of external apparatuses.

For example, if the determined body condition of the user is the normal condition, the processor 150 may continue to determine the body condition of the user by using the bio signals of the user without a separate notification or may control the communicator 130 to transmit the information about the measured body condition to a terminal apparatus of the user for healthcare of the user.

If the determined body condition of the user is the caution condition, the processor 150 may control the communicator 130 to transmit the information about the measured body condition to the terminal apparatus of the user to notify that the body condition of the user is beyond the normal condition.

If the determined body condition of the user is the danger condition, the processor 150 may control the communicator 130 to transmit the information about the measured body condition to at least one external apparatus designated by the user. For example, if the processor 150 determines the determined body condition of the user as the danger condition, the processor 150 may transmit the information about the measured body condition to a terminal apparatus of a family member of the user.

If the body condition of the user is the emergency condition, the processor 150 may transmit the information about the body condition of the user to an external apparatus arranged in a public center and may request a rescue. For example, if the body condition of the user is the emergency condition, the processor 150 may transmit the information about the body condition of the user to a server of an emergency center and may request a rescue.

The processor 150 may provide a notification while transmitting the information about the body condition of the user to at least one external apparatus.

Figure 3:
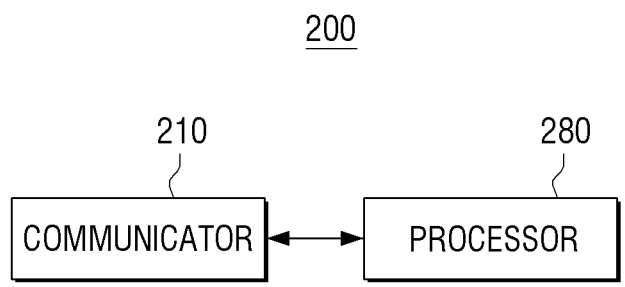
FIG. 3 is a block diagram of an electronic apparatus according to an embodiment of the present disclosure.

FIG. 3 is a block diagram of an electronic apparatus according to an embodiment of the present disclosure. For example, the electronic apparatus may be the terminal apparatus 200 of a user.

Referring to FIG. 3, the terminal apparatus 200 may include a communicator 210 and a processor 280.

The communicator 210 may use not only a form connected to an external apparatus over a LAN and the Internet but also wireless communication methods (for example, GSM, UMTS, LTE, WiBRO, WiFi, Bluetooth, etc.) in order to connect an external device, an external terminal, and the terminal apparatus 200 of the user.

For example, the communicator 210 may receive a plurality of bio signals of the user measured by the external device.

The communicator 210 may transmit information about a body condition of the user to the external apparatus corresponding to the body condition of the user determined based on the received plurality of bio signals of the user.

The processor 280 may control the communicator 210 to receive the measured plurality of bio signals of the user from the external device.

The processor 280 may determine the body condition of the user by using the received plurality of bio signals of the user. For example, the processor 280 may determine the body condition of the user as one of a normal condition, a caution condition, a danger condition, and an emergency condition based on the received plurality of bio signals.

The processor 280 may control the communicator 210 to transmit the information about the determined body condition of the user to the external apparatus corresponding to the determined body condition of the user among a plurality of external apparatuses. For example, if the body condition of the user is the caution condition, the processor 280 may display the information about the body condition of the user on a display provided in the terminal apparatus 200 of the user without transmitting the information about the body condition of the user to the external apparatus, if the body condition of the user is the danger condition, may transmit the information about the body condition of the user to a preset terminal apparatus of other, and, if the body condition of the user is the emergency condition, may transmit the information about the body condition of the user to an emergency center.

Although only the brief configuration of the terminal apparatus 200 of the user is illustrated and described above, various configurations may be additionally provided when implemented. This is described below in greater detail with reference to FIG. 4.

Figure 4:
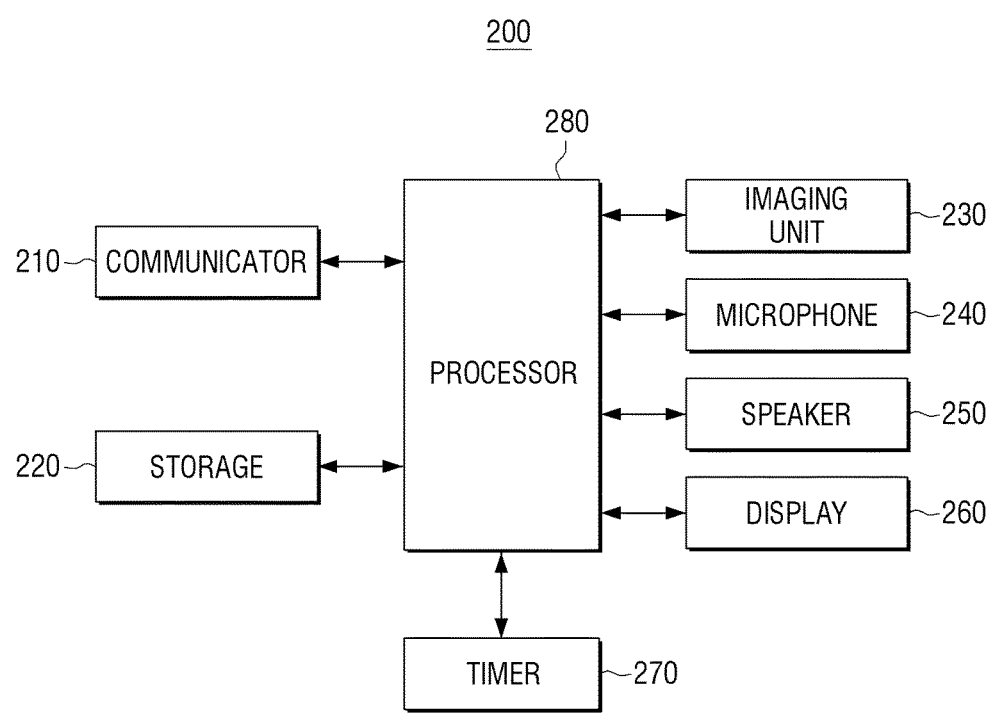
FIG. 4 is a block diagram of an electronic apparatus according to an embodiment of the present disclosure.

FIG. 4 is a block diagram of an electronic apparatus according to an embodiment of the present disclosure.

Referring to FIG. 4, the terminal apparatus 200 may include the communicator 210, a storage 220, an imaging unit 230, a microphone 240, a speaker 250, a display 260, a timer 270, and the processor 280.

The terminal apparatus 200 of a user may receive a plurality of bio signals of the user from an external device to determine a body condition of the user. In this regard, the terminal apparatus 200 of the user may transmit information about the body condition of the user to an external apparatus corresponding to the determined body condition of the user among a plurality of external terminals.

In this regard, the terminal apparatus 200 of the user may be a portable display apparatus of the user such as a smart phone, a tablet PC, a PMP, a PDA, a smart watch, etc. and may be a non-portable display apparatus of the user such as a smart TV, etc.

The communicator 210 may use the received plurality of bio signals to transmit the information about the body condition of the user determined by the processor 280 to at least one external apparatus corresponding to the body condition of the user.

If the body condition of the user is an emergency condition, if a time measured by the timer 270 provided in the terminal apparatus 200 of the user exceeds a preset time, the communicator 210 may transmit a notification to at least one external apparatus. For example, the communicator 210 may transmit the notification to an emergency center.

The communicator 210 may transmit at least one of an image generated by the imaging unit 230 provided in the terminal apparatus 200 of the user and voice information generated by the microphone 240 to the at least one external apparatus. For example, the communicator 210 may transmit at least one of the image and the voice information to the emergency center.

The storage 220 may store the plurality of bio signals of the user received from the external device. The storage 220 may use the plurality of bio signals received by the communicator 210 to store the information about the body condition of the user determined by the processor 280.

If the body condition of the user is the emergency condition, the storage 220 may store a time the emergency condition has started, a golden time for a rescue of the user, and a time the emergency center has arrived that are measured by the timer 270, the image generated by the imaging unit 230 and the voice information generated by the microphone 240.

The storage 220 may store disease information of the user input by the user and range setting information of a bio signal for determining the body condition of the user. In this regard, the range setting information of the bio signal may be a range set according to the disease information of the user or may be a range set by an input of the user.

The imaging unit 230 may generate an image. For example, the imaging unit 230 may operate if the body condition of the user is the emergency condition and generate an image if the user is in the emergency condition. In this regard, the imaging unit 230 may be a camera.

The microphone 240 may generate voice information. For example, the microphone 240 may operate if the body condition of the user is the emergency condition and generate a situation if the user is in the emergency condition as the voice information. For example, the microphone 240 may generate voice information if the user is in the emergency condition to allow the user to know information about whether the user fainted and got a big external shock.

The speaker 250 may provide a sound notification. For example, if the body condition of the user is the emergency condition, the speaker 250 may notify surrounding people of an emergency through sound to allow a rescue response to proceed.

The display 260 may display the information about the body condition of the user. For example, if the body condition of the user is the normal condition, the display 260 may use the plurality of bio signals received by the communicator 210 to display the information about the body condition of the user determined by the processor 280. Thus, the user may frequently monitor the body condition of the user to continuously care for the user's health.

The timer 270 may measure a time an emergency condition has started and an elapsed time if the body condition of the user is the emergency condition.

The processor 280 may determine the body condition of the user as one of a normal condition, a caution condition, a danger condition, and the emergency condition based on the received plurality of bio signals.

In this regard, if each of the received plurality of bio signals is within a normal range, the processor 280 may determine the body condition of the user as the normal condition. If at least one of the received plurality of bio signals is beyond the normal range, the processor 280 may determine the body condition of the user as the caution condition. The caution condition may be a condition in which a numerical value of a bio signal does not belong to the normal range but does not directly affect the life of the user.

If at least each of the measured plurality of bio signals is beyond the normal range and a complication symptom is sensed, the processor 280 may determine the body condition of the user as the danger condition. For example, if a diabetic having blood glucose beyond a normal range has a high blood pressure symptom, the processor 280 may determine a body condition of the diabetic as the danger condition.

If the user corresponding to the danger condition has an emergency disease, the processor 280 may determine the body condition of the user as the emergency condition. For example, if heartbeat or respiration of a diabetic having a complication symptom is beyond the normal range, the processor 280 may determine the body condition of the diabetic as the emergency condition.

The processor 280 may determine the body condition of the user in consideration of previously stored disease information of the user. For example, the processor 150 may apply a body condition determination standard of the user differently according to previously input disease information of the user. For example, with regard to blood pressure among the plurality of bio signals, if the blood pressure of the user who is a normal person ranges from 140 mmHg to 90 mmHg, the processor 280 may determine the body condition of the user as the normal condition while only if the blood pressure of the user who is a diabetic ranges from 120 mmHg to 80 mmHg, the processor 280 may determine the body condition of the user as the normal condition. That is, if the blood pressure of a diabetic is within a normal range of a normal person from 140 mmHg to 90 mmHg but is beyond the range from 120 mmHg to 80 mmHg, the processor 280 may determine the body condition of the user as the danger condition.

The processor 280 may determine the body condition of the user by using a first group of bio signals among the plurality of bio signals received from an external device by the communicator 210 if a preset condition is satisfied. The processor 280 may determine the body condition of the user by further using a second group of bio signals among the plurality of bio signals if the preset condition is not satisfied.

In this regard, the preset condition may be that preset measurement values of the first group of bio signals are all within a normal range. In this regard, if preset at least one measurement value of the first group of bio signals is beyond the normal range, the processor 280 may determine the body condition of the user by further using the second group of bio signals.

In this regard, the first group of bio signals among the plurality of bio signals may be bio signals that are related to basal metabolism and disease of the user and need to be continuously monitored in daily life. The second group of bio signals may be bio signals directly related to the life of the user. For example, the first group of bio signals may be at least one of blood glucose, blood pressure, ECG, pulse, and cholesterol, and the second group of bio signals may be at least one of respiration, heartbeat, and body temperature. However, this is merely an example. The plurality of bio signals may be divided into three or more groups and measured.

The processor 280 may determine the body condition of the user by receiving only the first group of bio signals among the plurality of bio signals if the preset condition is satisfied, and may request the external device to further transmit the second group of bio signals if the preset condition is not satisfied. In this regard, the processor 280 may further receive the second group of bio signals measured by the external device to determine the body condition of the user.

The processor 280 may control the communicator 210 to transmit information about the measured body condition to a corresponding external apparatus according to the determined body condition of the user among a plurality of external apparatuses.

For example, if the determined body condition of the user is the normal condition, the processor 280 may continue to determine the body condition of the user based on the bio signals of the user without a separate operation. In this regard, the processor 280 may display the information about the body condition of the user on the display 260 provided in the terminal apparatus 200 of the user for continuous healthcare of the user.

If the determined body condition of the user is the caution condition, the processor 280 may display the information about the measured body condition on the display 260 provided in the terminal apparatus 200 of the user to notify that the body condition of the user is beyond the normal condition.

If the determined body condition of the user is the danger condition, the processor 280 may control the communicator 210 to transmit the information about the measured body condition to at least one external apparatus designated by the user. For example, if the processor 280 determines the determined body condition of the user as the danger condition, the processor 280 may transmit the information about the body condition of the user to a terminal apparatus of a family member of the user.

If the body condition of the user is the emergency condition, the processor 280 may transmit the information about the body condition of the user to an external apparatus arranged in a public center and may request a rescue. For example, if the body condition of the user is the emergency condition, the processor 280 may transmit the information about the body condition of the user to a server of an emergency center and may request a rescue.

The processor 280 may provide a notification while displaying the information about the body condition of the user on the display 260 or transmitting the information about the body condition of the user to at least one external apparatus.

If the body condition of the user is the emergency condition, the processor 280 may operate at least one of the imaging unit 230 and the microphone 240 and may control the communicator 210 to transmit at least one of the image generated by the imaging unit 230 and the voice information generated by the microphone 240 to the at least one external apparatus.

If the body condition of the user is the emergency condition, the processor 280 may operate the timer 270 to measure a time the emergency condition started and an elapsed time, and, if the emergency condition continues for more than a preset time, may control the communicator 210 to transmit a notification to the emergency center. When practically implemented, the processor 280 may set an emergency condition continuation time in stages and may control the communicator 210 to transmit a plurality of notifications to the emergency center according to the emergency condition continuation time.

Therefore, the user may frequently check the information about the body condition of the user in daily life to continuously care about the user's health, and a quick rescue response may be made if an emergency occurs in the user.

Figure 5:
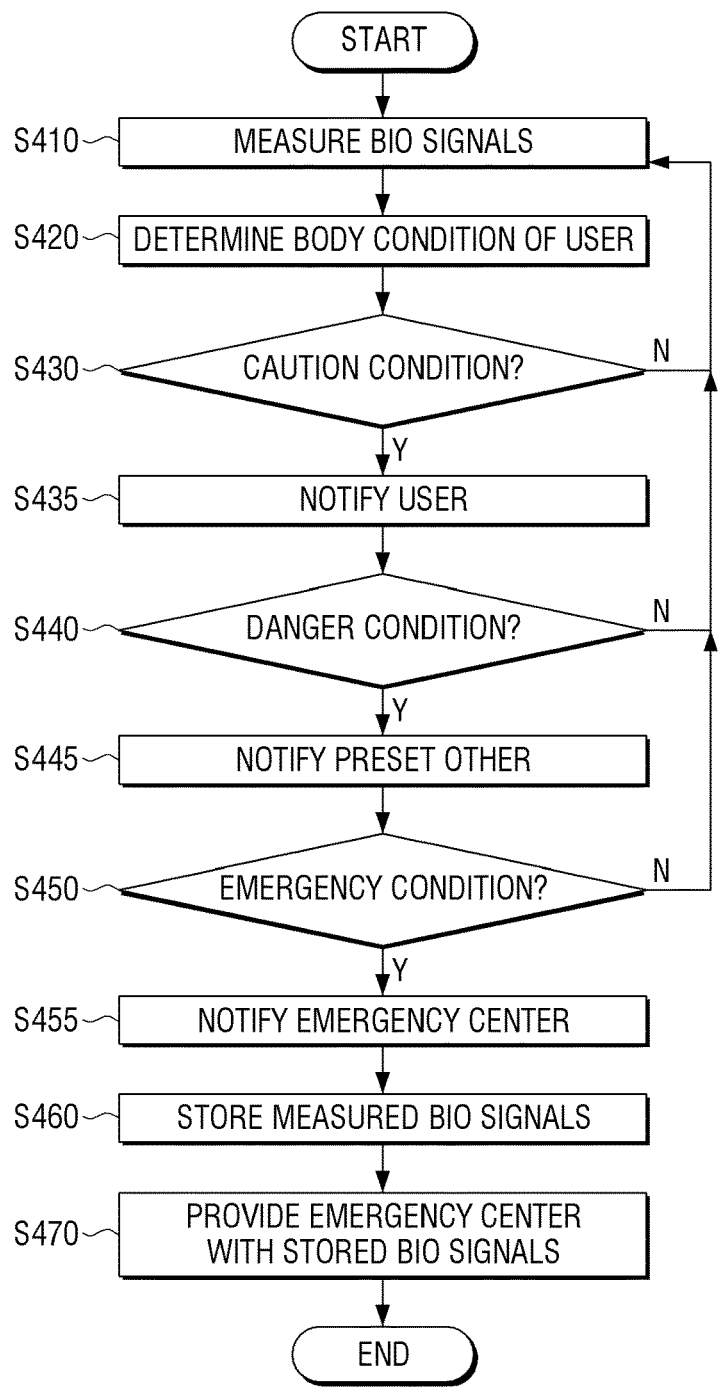
FIGS. 5 and 6 are flowcharts of a user body monitoring process performed in stages according to a body condition of a user according to an embodiment of the present disclosure.

FIG. 5 is a flowchart of a user body monitoring process performed in stages according to a body condition of a user.

Referring to FIG. 5, an external device may measure a plurality of bio signals of a user in step S410. Thereafter, an electronic apparatus according to an embodiment of the present disclosure may receive the plurality of bio signals of the user measured by the external device. If the electronic apparatus is the external device that measures the plurality of bio signals of the user, the electronic apparatus may monitor a user's body by using the measured plurality of bio signals without a separate process of transmitting the measured plurality of bio signals. An embodiment of the present disclosure in which the electronic apparatus is the external device that measures the plurality of bio signals of the user is described below in greater detail with reference to FIG. 12.

Thereafter, the electronic apparatus may determine a body condition of the user by using the received plurality of bio signals in step S420. In this regard, the electronic apparatus may determine the body condition of the user as a normal condition or a condition beyond the normal condition according to the received plurality of bio signals. For example, the electronic apparatus may determine the condition beyond the normal condition of the body condition of the user as one of a caution condition, a danger condition, and an emergency condition. For convenience of description, the case where the body condition of the user is the condition beyond the normal condition is limited and described below. For example, the electronic apparatus may determine the body condition of the user as a caution condition in step S430. In this regard, if at least one of the received plurality of bio signals is beyond a normal range, the electronic apparatus may determine the body condition of the user as the caution condition.

In this regard, if the body condition of the user is not the caution condition in step S430, the electronic apparatus may determine the body condition of the user as the normal condition, may receive the bio signals of the user without a separate operation, and may determine the body condition of the user.

If the body condition of the user is the caution condition in step S430, the electronic apparatus may provide a notification to the user in step S435. For example, the electronic apparatus may provide information about the body condition of the user to the user. In this regard, if the electronic apparatus is a terminal apparatus of the user, the electronic apparatus may display the information about the body condition of the user on the terminal apparatus to provide the user with the information. If the electronic apparatus is not the terminal apparatus of the user but is a terminal apparatus of another, a server, an Internet sharer, and the external device that measures the bio signals of the user, the electronic apparatus may transmit the information about the body condition of the user to the terminal apparatus of the user to provide the user with the information. Therefore, the user may frequently monitor the body condition of the user in daily life to continuously care for the health of the user.

Thereafter, the electronic apparatus may determine if the body condition of the user is a danger condition in step S440. In this regard, if each of the received plurality of bio signals is beyond the normal range and a complication symptom is sensed, the electronic apparatus may determine the body condition of the user as the danger condition.

If the body condition of the user is the danger condition in step S440, the electronic apparatus may provide another who is preset with a notification in step S445. For example, if the body condition of the user is determined to be the danger condition, the electronic apparatus may transmit the information about the body condition of the user to another who is preset and who is a family member of the user. Therefore, prevention and a quicker measure may be prepared before the body condition of the user becomes an emergency condition.

If the body condition of the user is not the danger condition in step S440, the electronic apparatus may continuously determine the body condition of the user by using the received bio signals of the user.

Thereafter, the electronic apparatus may determine whether the body condition of the user is an emergency condition in step S450. In this regard, if the user corresponding to the danger condition has an emergency disease, the electronic apparatus may determine the body condition of the user as the emergency condition.

If the body condition of the user is the emergency condition in step S450, the electronic apparatus may provide an emergency center with a notification in step S455. If at least one of the plurality of bio signals (for example, respiration, heartbeat, pulse, etc.) directly related to life among the bio signals of the user corresponding to the emergency condition is beyond the normal range, the electronic apparatus may determine the body condition of the user as the emergency condition and transmit the information about the body condition of the user and a rescue request to an emergency center.

If the body condition of the user is not the emergency condition in step S450, the electronic apparatus may continuously determine the body condition of the user by using the received bio signals of the user.

Thereafter, the electronic apparatus may continuously measure the plurality of bio signals of the user to store the measured plurality of bio signals in step S460. In this regard, the electronic apparatus may measure and store not only the plurality of bio signals but also a time an emergency condition started and an elapsed time, an image and voice information that enables the identification of a situation of the emergency condition. An operation of the electronic apparatus if the body condition of the user is the emergency condition is described below in greater detail with reference to FIG. 7.

Thereafter, if the emergency center arrives at the user, the electronic apparatus may provide the stored plurality of bio signals to the emergency center in step S470. In this regard, the electronic apparatus may provide the stored plurality of bio signals by transmitting the stored plurality of bio signals to the emergency center or by displaying the information about the body condition of the user on a display provided in the electronic apparatus. Although it is limited and described that the stored plurality of bio signals are provided to the emergency center, when practically implemented, the measured plurality of bio signals may be provided to the emergency center. Therefore, if the body condition of the user is the emergency condition, the electronic apparatus may quickly call the emergency center and take a more prompt measure, thereby preventing the condition of a patient from deteriorating.

Figure 6:
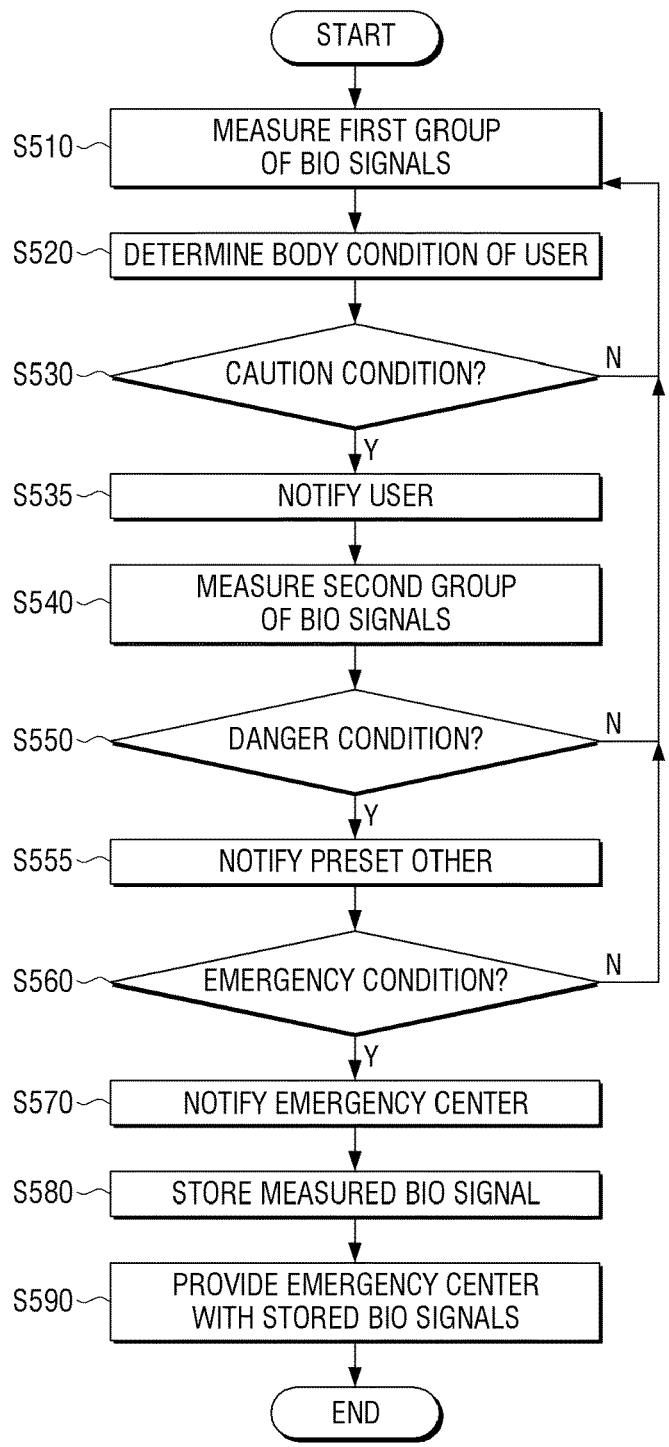

FIG. 6 is a flowchart of a user body monitoring process performed in stages according to a body condition of a user according to an embodiment of the present disclosure.

Referring to FIG. 6, an external device may measure a first group of bio signals among a plurality of bio signals of the user in step S510. Thereafter, an electronic apparatus may receive the first group of bio signals measured by the external device. If the electronic apparatus is the external device that measures the first group of bio signals of the user, the electronic apparatus may monitor a user's body by using the measured bio signals without a separate process of transmitting the measured first group of bio signals. An embodiment of the present disclosure in which the electronic apparatus is the external device that measures the bio signals of the user is described below in detail with reference to FIG. 11.

Thereafter, the electronic apparatus may determine a body condition of the user by using the received first group of bio signals in step S520. For example, the electronic apparatus may determine the body condition of the user as a caution condition according to the received first group of bio signals in step S530. In this regard, if at least one of the received plurality of bio signals is beyond a normal range, the electronic apparatus may determine the body condition of the user as the caution condition.

In this regard, if the body condition of the user is not the caution condition in step S530, the electronic apparatus may determine the body condition of the user as a normal condition, may receive the bio signals of the user without a separate operation, and may determine the body condition of the user.

If the body condition of the user is the caution condition in step S530, the electronic apparatus may provide a notification to the user in step S535. For example, the electronic apparatus may provide information about the body condition of the user to the user. In this regard, if the electronic apparatus is a terminal apparatus of the user, the electronic apparatus may display the information about the body condition of the user on the terminal apparatus to provide the user with the information. If the electronic apparatus is not the terminal apparatus of the user but is a terminal apparatus of another, a server, an Internet sharer, and the external device that measures the bio signals of the user, the electronic apparatus may transmit the information about the body condition of the user to the terminal apparatus of the user to provide the user with the information. Therefore, the user may frequently monitor the body condition of the user in daily life to continuously care for the health of the user.

Thereafter, the external device connected to the electronic apparatus may measure a second group of bio signals in step S540. In this regard, the external device may receive a request to transmit the second group of bio signals from the electronic apparatus and may measure the second group of bio signals. If the electronic apparatus according to an embodiment of the present disclosure is the external device that measures the first group of bio signals of the user, the electronic apparatus may measure the second group of bio signals without a separate request process.

Thereafter, the electronic apparatus may receive the second group of bio signals measured by the external device. If the electronic apparatus is the external device that measures the second group of bio signals of the user, the electronic apparatus may monitor the body of the user by using the measured bio signals without a separate process of transmitting the measured second group of bio signals. As such, the plurality of bio signals may be divided into groups and measured in stages, thereby reducing power of the external device that measures the plurality of bio signals and increasing a transmission speed of the measured bio signals.

Thereafter, the external device connected to the electronic apparatus may determine if the body condition of the user is a danger condition in step S550. In this regard, if at least each of the received plurality of bio signals is beyond the normal range and a complication symptom is sensed, the electronic apparatus may determine the body condition of the user as the danger condition. For example, if at least each of the first group of bio signals is beyond the normal range and at least each of the second group of bio signals related to the complication symptom is beyond the normal range, the electronic apparatus may determine the body condition of the user as the danger condition.

If the body condition of the user is the danger condition in step S550, the electronic apparatus may provide another who is preset with a notification in step S555. For example, if the body condition of the user is determined to be the danger condition, the electronic apparatus may transmit the information about the body condition of the user to another who is preset and who is a family member of the user. Therefore, prevention and a quicker measure may be prepared before the body condition of the user becomes the emergency condition.

If the body condition of the user is not the danger condition in step S550, the electronic apparatus may continuously determine the body condition of the user by using the received bio signals of the user.

Thereafter, the electronic apparatus may determine whether the body condition of the user is an emergency condition in step S560. In this regard, if the user corresponding to the danger condition has an emergency disease, the electronic apparatus may determine the body condition of the user as the emergency condition.

If the body condition of the user is the emergency condition in step S560, the electronic apparatus may provide an emergency center with a notification in step S570. If at least one of the plurality of bio signals (for example, respiration, heartbeat, pulse, etc.) directly related to life among the bio signals of the user corresponding to the emergency condition is beyond the normal range, the electronic apparatus may determine the body condition of the user as the emergency condition and transmit the information about the body condition of the user and a rescue request to an emergency center.

If the body condition of the user is not the emergency condition in step S560, the electronic apparatus may continuously determine the body condition of the user by using the received bio signals of the user.

Thereafter, the electronic apparatus may continuously measure the plurality of bio signals of the user included in the first group and the second group to store the measured plurality of bio signals in step S580. In this regard, the electronic apparatus may measure and store not only the plurality of bio signals but also a time that an emergency condition started and an elapsed time, and an image and voice information that enables the identification of the emergency condition. An operation of the electronic apparatus if the body condition of the user is the emergency condition is described below in greater detail with reference to FIG. 7.

Thereafter, if the emergency center arrives at the user, the electronic apparatus may provide the stored plurality of bio signals to the emergency center in step S590. In this regard, the electronic apparatus may provide the stored plurality of bio signals by transmitting the stored plurality of bio signals to the emergency center or by displaying the information about the body condition of the user on a display provided in the electronic apparatus. Although it is limited and described that the stored plurality of bio signals are provided to the emergency center, when practically implemented, the measured plurality of bio signals may be immediately provided to the emergency center. Therefore, if the body condition of the user is the emergency condition, the electronic apparatus may quickly call the emergency center and take a more prompt measure, thereby preventing the condition of a patient from deteriorating.

Figure 7:
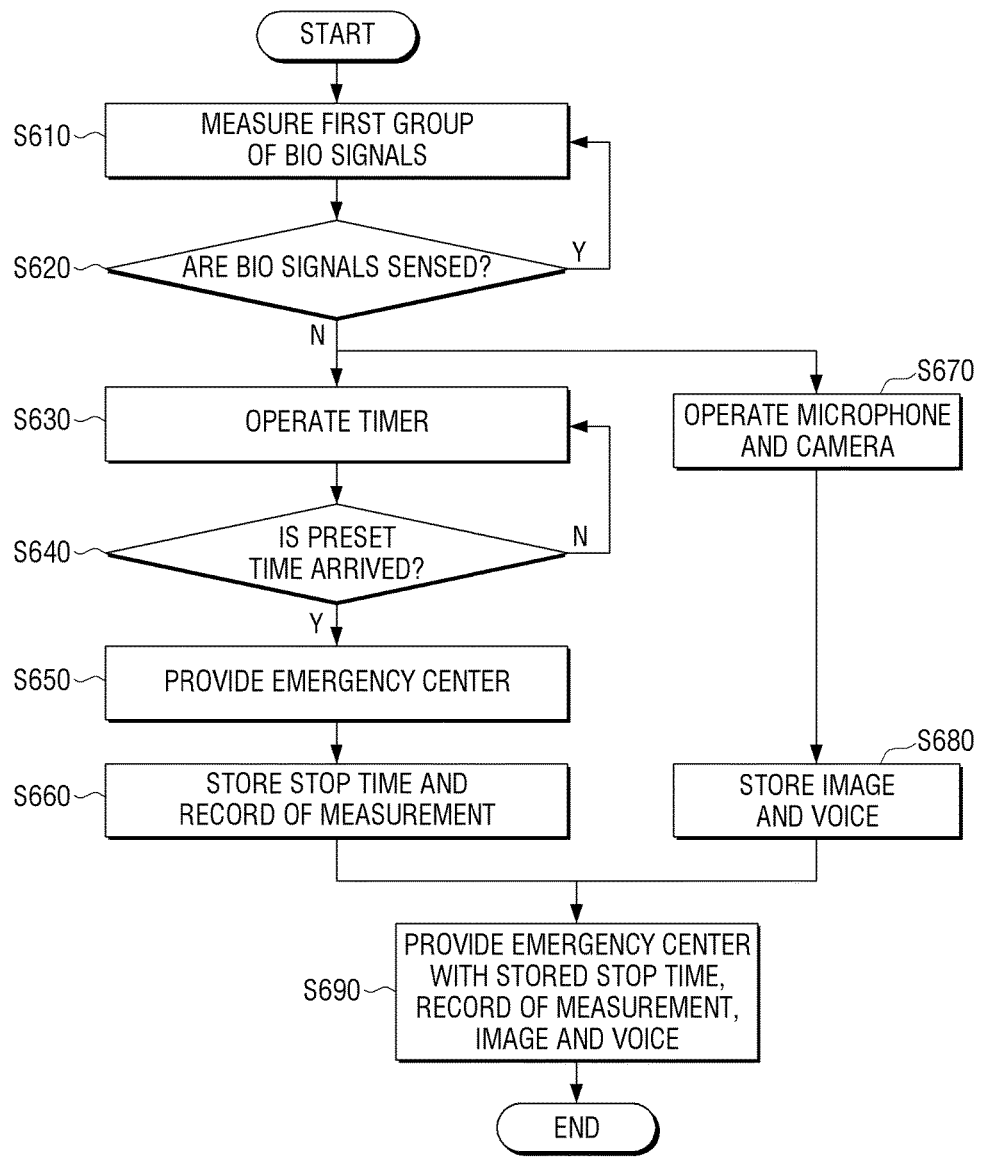
FIG. 7 is a flowchart of a user body monitoring process performed if an emergency occurs according to an embodiment of the present disclosure.

FIG. 7 is a flowchart of a user body monitoring process performed if an emergency occurs according to an embodiment of the present disclosure.

Referring to FIG. 7, an external device may measure a plurality of bio signals of a user in step S610. Thereafter, an electronic apparatus may receive the measured plurality of bio signals from the external device. Thereafter, the electronic apparatus may determine whether the plurality of bio signals are sensed in step S620. In this regard, whether the plurality of bio signals are sensed may indicate whether at least one of the plurality of bio signals is stopped. The electronic apparatus may use the measured plurality of bio signals of the user to determine whether a body condition of the user is an emergency condition.

In this regard, if all of the plurality of bio signals are sensed in step S620, the electronic apparatus may continue to receive the bio signals measured by the external device to determine the body condition of the user. If at least one of the plurality of bio signals is stopped in step S620 or if the body condition of the user is the emergency condition, the electronic apparatus may operate a timer in step S630. For example, the electronic apparatus may operate the timer to measure at least one of a time the at least one of the plurality of bio signals is stopped and an elapsed time, a time the body condition of the user is the emergency condition, and an elapsed time.

Thereafter, the electronic apparatus may determine if a preset time is reached from the time the at least one signal is stopped and the time the body condition of the user is the emergency condition in step S640. In this regard, if the preset time is not reached in step S640, the electronic apparatus may continue to measure a time elapsed from the time the at least one signal is stopped and the time the body condition of the user is the emergency condition. If the preset time is reached in step S640, the electronic apparatus may provide an emergency center with a notification in step S650. For example, the electronic apparatus may transmit information about the body condition of the user and a rescue request to the emergency center. Although it is limited and described that a time set to send the notification to the emergency center is one, when practically implemented, a plurality of times may be set to provide the emergency center with the notification in stages over time.

Thereafter, the electronic apparatus may store the time the at least one of the plurality of bio signals is stopped, the time the body condition of the user is the emergency condition, and a record of the measured time elapsed from the time in step S660.

Thereafter, if the emergency center arrives at the user, the electronic apparatus may provide the emergency center with the stored time the at least one of the plurality of bio signals is stopped and the time the body condition of the user is the emergency condition, and the time elapsed from the time in step S690. In this regard, the electronic apparatus may provide the emergency center with the stored stop time and the record of measurement by transmitting the stored stop time and the record of measurement to the emergency center or by displaying the stored stop time and the record of measurement on a display provided in the electronic apparatus. Therefore, if the body condition of the user is the emergency condition, the electronic apparatus may quickly call the emergency center and take a more prompt measure than a golden time, thereby preventing the condition of a patient from deteriorating.

If the at least one of the plurality of bio signals of the user is stopped in step S620 or if the body condition of the user is the emergency condition, the electronic apparatus may operate at least one of a microphone and a camera in step S670. For example, the electronic apparatus may operate at least one of the camera that generates an image and the microphone that generates voice information.

Thereafter, the electronic apparatus may store at least one of the generated image and voice information in step S680. Thereafter, if the emergency center arrives at the user, the electronic apparatus may provide the emergency center with the stored image and voice information in step S690. In this regard, the electronic apparatus may provide the emergency center with the stored image and voice information by transmitting the stored image and voice information to the emergency center or by displaying the stored image on the display provided in the electronic apparatus and outputting the voice information through a speaker. Therefore, if at least one of the plurality of bio signals of the user is stopped or the body condition of the user is the emergency condition, a situation of the user such as whether there is an external shock, etc. may be known, thereby facilitating the rescue of the user.

Figure 8:
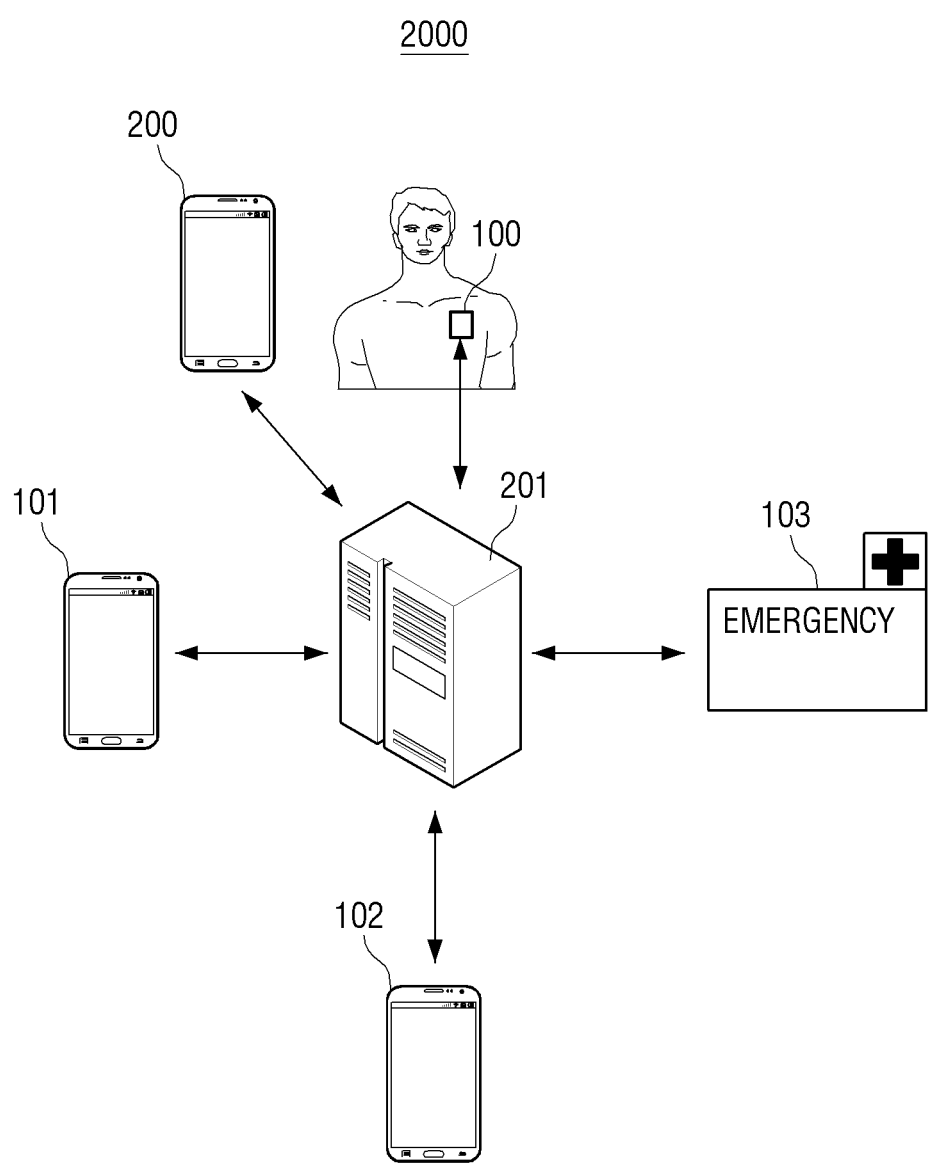
FIG. 8 illustrates a user body monitoring system using a server according to an embodiment of the present disclosure.

FIG. 8 illustrates a user body monitoring system 2000 using an electronic apparatus according to an embodiment of the present disclosure. For example, the electronic apparatus may be a server.

Referring to FIG. 8, the user body monitoring system 2000 using the electronic apparatus may include the external device 100 attached to a user's body, the terminal apparatus 200 of the user, the terminal apparatuses 101 and 102 of others, the emergency center 103, and a server 201.

In this regard, the external device 100 attached to the body of the user may measure a plurality of bio signals of the user. For example, the external device 100 may be attached to the body of the user with adhesion to measure the plurality of bio signals related to a basal metabolism of the user and a bio signal directly related to the life of the user. The external device 100 may transmit the measured plurality of bio signals of the user to the server 201. A detailed configuration of the external device 100 is described below with reference to FIG. 2 above.

In this regard, the external device 100 attached to the body of the user may be a patch type device that measures the plurality of bio signals of the user. For example, the external device 100 may be the patch type device including a sensor for measuring the plurality of bio signals of the user.

Although the external device 100 attached to the body of the user is limited, illustrated, and described as the patch type device for convenience of description, the external device 100 may be a band type device wearable on a part of the body of the user without adhesion when practically implemented.

Although the external device 100 is described as one external device for convenience of description, a plurality of external devices may be used to measure bio signals of the user when practically implemented.

The server 201 may receive the measured plurality of bio signals of the user from the external device 100. In this regard, the server 201 may use the received plurality of bio signals to determine a body condition of the user. For example, the server 201 may determine the body condition of the user as one of a normal condition, a caution condition, a danger condition, and an emergency condition.

The server 201 may transmit information about the body condition of the user to an external apparatus corresponding to the determined body condition of the user among the plurality of external apparatuses 200, 101, 102, and 103. For example, if the server 201 determines the body condition of the user as the normal condition, the server 201 may continue to determine the body condition of the user based on the received bio signal of the user without a separate operation. In this regard, the server 201 may transmit the information about the body condition of the user to the terminal apparatus 200 of the user for continuous healthcare of the user.

If the body condition of the user is the caution condition, the server 201 may transmit the information about the body condition of the user to the terminal apparatus 200 of the user to notify the user that the body condition of the user is beyond the normal condition.

If the server 201 determines the body condition of the user as the danger condition, the server 201 may transmit the information about the body condition of the user to the at least one external apparatuses 101 and 102 designated by the user. For example, if the server 201 determines the body condition of the user as the danger condition, the server 201 may transmit the information about the body condition of the user to the terminal apparatuses 101 and 102 of family members of the user.

If the body condition of the user is the emergency condition, the server 201 may transmit the information about the body condition of the user to the external apparatus 103 arranged in a public center and may request a rescue. For example, if the body condition of the user is the emergency condition, the server 201 may transmit the information about the body condition of the user to the server 103 of the emergency center and may request a rescue.

In addition, the server 201 may provide a notification while transmitting the information about the body condition of the user to the plurality of external apparatuses 200, 101, 102, and 103.

Although the plurality of external apparatuses 200, 101, and 102 are limited, illustrated, and described as terminal apparatuses of the user and others designated by the user for convenience of description, the plurality of external apparatuses 200, 101, and 102 may be a display apparatus such as a smart TV, a tablet PC, a PMP, a PDA, a smart watch, etc. when practically implemented.

Although the external device 100 that measures the bio signal of the user and the terminal apparatus 200 of the user are illustrated and described to be spaced apart from each other in FIG. 8 for convenience of description, the external device 100 and the terminal apparatus 200 of the user may be an all-in-one type when practically implemented. For example, if the terminal apparatus 200 of the user is a smart watch, a wrist band part of the smart watch in contact with the body of the user may be implemented to include the external device 100 that measures the bio signal of the user.

Figure 9:
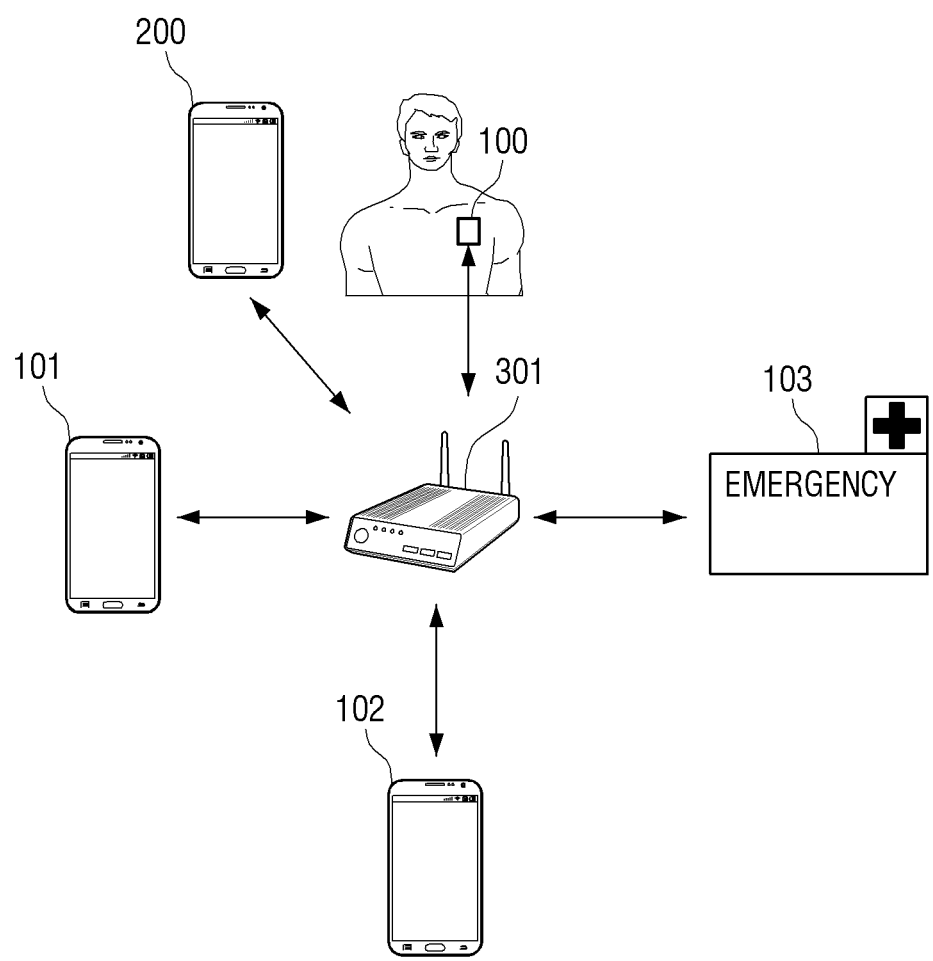
FIG. 9 illustrates a user body monitoring system using a sharer according to an embodiment of the present disclosure.

FIG. 9 illustrates a user body monitoring system 3000 using an electronic apparatus according to an embodiment of the present disclosure. For example, the electronic apparatus may be an Internet sharer.

Referring to FIG. 9, the user body monitoring system 3000 using the electronic apparatus may include the external device 100 attached to a user's body, the terminal apparatus 200 of the user, the terminal apparatuses 101 and 102 of others, the emergency center 103, and an Internet sharer 301.

In this regard, the external device 100 attached to the body of the user may measure a plurality of bio signals of the user. The external device 100 attached onto the body of the user is the same as the external device 100 shown in FIGS. 1 and 8, and thus a detailed description thereof is omitted.

If the external device 100 is in a sleep mode, the Internet sharer 301 may monitor a user's body.

For example, the Internet sharer 301 may transmit and receive a wireless communication signal to and from the external device 100 that measures the plurality of bio signals of the user. For example, the Internet sharer 301 may receive the wireless communication signal from the external device 100 to determine whether the external device 100 moves. A method of determining a movement of the external device 100 using the wireless communication signal is described below in greater detail with reference to FIG. 10.

The Internet sharer 301 may transmit a request to the external device 100 attached to the body of the user to measure and transmit the plurality of bio signals. For example, if the external device 100 is in the sleep mode, and if the Internet sharer 301 does not sense the movement of the external device 100 for a preset time, the Internet sharer 301 may transmit the request to the device 100 to transmit the plurality of bio signals of the user.

The sleep mode of the external device 100 may be a status in which it is possible to transmit and receive the wireless communication signal with the Internet sharer 301 or an external apparatus while the plurality of bio signals of the user are not measured in order to reduce power consumption of the external device 100.

The external device 100 may be changed to an active mode according to a request of the Internet sharer 301 to measure the plurality of bio signals of the user, and the Internet sharer 301 may receive the plurality of bio signals of the user measured by the external device 100.

The Internet sharer 301 may use the received plurality of bio signals to determine a body condition of the user. For example, the Internet sharer 301 may determine the body condition of the user as one of a normal condition, a caution condition, a danger condition, and an emergency condition.

The Internet sharer 301 may transmit information about the body condition of the user to an external apparatus corresponding to the determined body condition of the user among the plurality of external apparatuses 200, 101, 102, and 103. For example, if the Internet sharer 301 determines the body condition of the user as the normal condition, the Internet sharer 301 may continue to determine the body condition of the user based on the received bio signal of the user without a separate operation. In this regard, the Internet sharer 301 may transmit the information about the body condition of the user to the terminal apparatus 200 of the user for continuous healthcare of the user.

If the body condition of the user is the caution condition, the Internet sharer 301 may transmit the information about the body condition of the user to the terminal apparatus 200 of the user to notify the user that the body condition of the user is beyond the normal condition.

If the Internet sharer 301 determines the body condition of the user as the danger condition, the Internet sharer 301 may transmit the information about the body condition of the user to the at least one external apparatuses 101 and 102 designated by the user. For example, if the Internet sharer 301 determines the body condition of the user as the danger condition, the Internet sharer 301 may transmit the information about the body condition of the user to the terminal apparatuses 101 and 102 of family members of the user.

If the body condition of the user is the emergency condition, the Internet sharer 301 may transmit the information about the body condition of the user to the external apparatus 103 arranged in a public center and may request a rescue. For example, if the body condition of the user is the emergency condition, the Internet sharer 301 may transmit the information about the body condition of the user to the server 103 of the emergency center and may request a rescue.

In addition, the Internet sharer 301 may provide a notification while transmitting the information about the body condition of the user to the plurality of external apparatuses 200, 101, 102, and 103.

If the external device 100 attached to the body of the user is in the sleep mode, the electronic apparatus may monitor the body of the user, thereby reducing power consumption of the external device 100.

Figure 10:
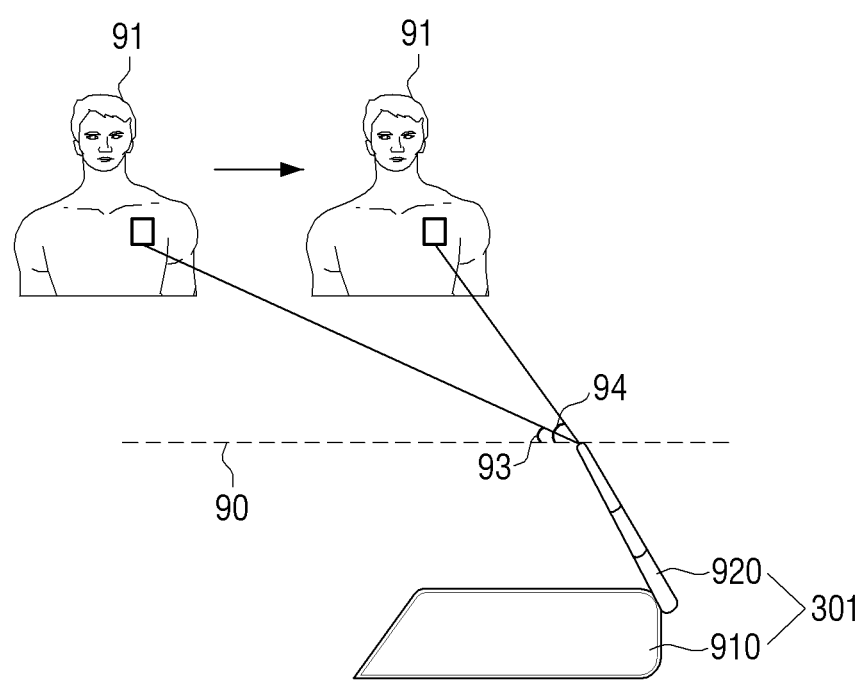
FIG. 10 illustrates a process of sensing a movement of a user by using a sharer according to an embodiment of the present disclosure.

FIG. 10 illustrates a process of sensing a movement of a user by using the Internet sharer 301 according to an embodiment of the present disclosure.

Referring to FIG. 10, the Internet sharer 301 may include a main body 910 and an antenna 920. In this regard, the main body 910 of the Internet sharer 301 may use a wireless communication signal to determine whether a user moves. For example, the main body 910 of the Internet sharer 301 may analyze the wireless communication signals received from an external device of the user through the antenna 920 to determine whether the user having the external device attached onto the body moves.

For example, the main body 910 of the Internet sharer 301 may use changes in angles 93 and 94 between a direction of the wireless communication signal received from the external device of the user through the antenna 920 and a line 90 in parallel to a ground surface to determine whether the user moves. For example, the main body 910 of the Internet sharer 301 may determine whether the user moves by comparing the angle 93 between the direction of the wireless communication signal received from the external device of a user 91 before movement and the line 90 in parallel to the ground surface and the angle 94 between the direction of the wireless communication signal received from the external device of the user 91 after movement and the line 90 in parallel to the ground surface.

Figure 11:
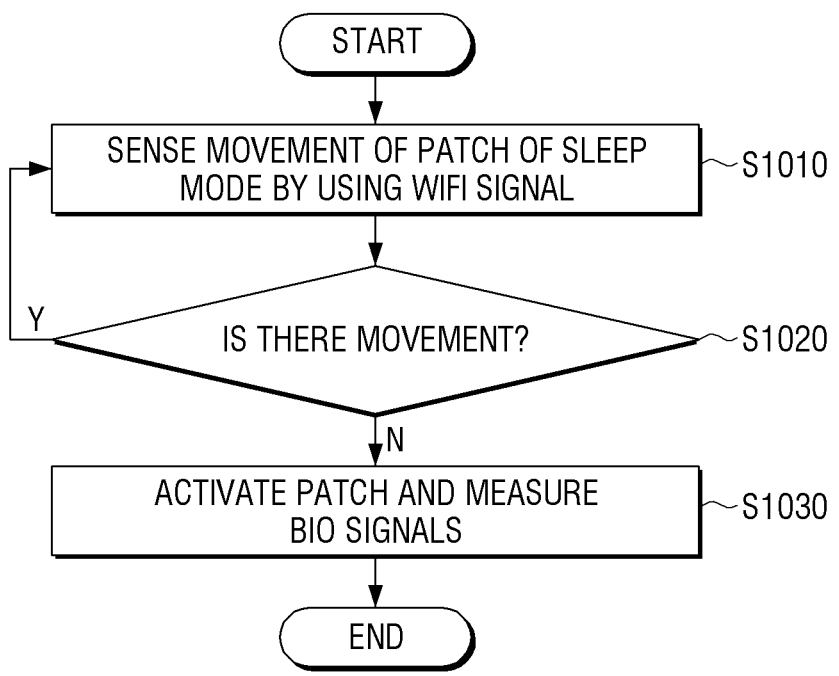
FIG. 11 is a flowchart of a process of monitoring a user's health by using a sharer according to an embodiment of the present disclosure.

FIG. 11 is a flowchart of a process of monitoring a user's health by using an Internet sharer according to an embodiment of the present disclosure.

Referring to FIG. 11, the Internet sharer may sense a movement of an external device in a sleep mode using a wireless communication signal (WiFi) in step S1010. In this regard, the external device in the sleep mode may be a patch type device that is directly attached to a body of the user and measures a plurality of bio signals of the user. Thereafter, the Internet sharer may determine whether the user moves in step S1020. A method of determining whether the user moves using the Internet sharer is described above with reference to FIG. 10.

In this regard, if a movement of the user is sensed in step S1020, the Internet sharer may continue to sense the movement of the user. If the movement of the user is not sensed in step S1020, the Internet sharer may receive a request for the external device in the sleep mode to change from the sleep mode to an active mode and transmit the bio signals. In this regard, the external device may change the sleep mode to the active mode according to the request of the Internet sharer and measure the plurality of bio signals of the user in step S1030. Thereafter, a process of monitoring the health of the user by using the plurality of bio signals measured by the external device is the same as described above with reference to FIGS. 5 and 6, and thus a detailed description thereof is omitted.

The plurality of bio signals of the user may be measured by activating the external device in the sleep mode only if the movement of the user is not sensed for a preset time by using the wireless communication signal, thereby reducing power consumption of the external device.

Figure 12:
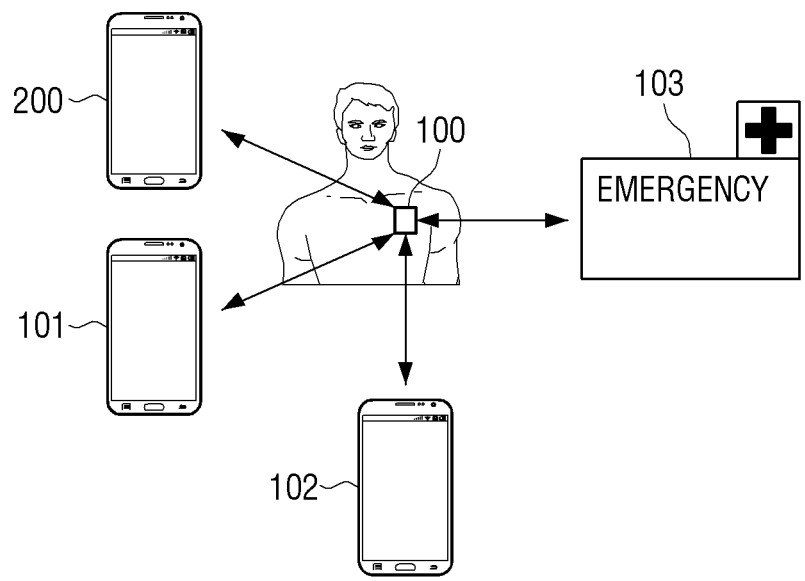
FIG. 12 illustrates a user body monitoring system using a patch attached to a body of a user according to an embodiment of the present disclosure.

FIG. 12 illustrates a user body monitoring system 4000 using an electronic apparatus according to an embodiment of the present disclosure. For example, the electronic apparatus may be an external device that is attached to a body of a user and measures a plurality of bio signals of the user.

Referring to FIG. 12, the user body monitoring system 4000 using the electronic apparatus may include the external device 100 attached to the body of the user, the terminal apparatus 200 of the user, the terminal apparatuses 101 and 102 of others, and the emergency center 103.

In this regard, the external device 100 attached to the body of the user may measure the plurality of bio signals of the user. An operation of the external device 100 attached to the body of the user to measure the plurality of bio signals of the user is the same as the external device 100 described above and shown in FIGS. 1 and 8, and thus a detailed description thereof is omitted.

The external device 100 attached to the body of the user may use the measured plurality of bio signals to determine a body condition of the user. For example, the external device 100 may determine the body condition of the user as one of a normal condition, a caution condition, a danger condition, and an emergency condition based on the measured plurality of bio signals.

The external device 100 may transmit information about the body condition of the user to an external apparatus corresponding to the determined body condition of the user among the plurality of external apparatuses 200, 101, 102, and 103. For example, if the external device 100 determines the body condition of the user as the normal condition, the Internet sharer 301 may continue to determine the body condition of the user based on the received bio signal of the user without a separate operation. In this regard, the external device 100 may transmit the information about the body condition of the user to the terminal apparatus 200 of the user for continuous healthcare of the user.

If the body condition of the user is the caution condition, the external device 100 may transmit the information about the body condition of the user to the terminal apparatus 200 of the user to notify the user that the body condition of the user is beyond the normal condition.

If the external device 100 determines the body condition of the user as the danger condition, the external device 100 may transmit the information about the body condition of the user to the at least one external apparatuses 101 and 102 designated by the user. For example, if the external device 100 determines the body condition of the user as the danger condition, the external device 100 may transmit the information about the body condition of the user to the terminal apparatuses 101 and 102 of family members of the user.

If the body condition of the user is the emergency condition, the external device 100 may transmit the information about the body condition of the user to the external apparatus 103 arranged in a public center and may request a rescue. For example, if the body condition of the user is the emergency condition, the external device 100 may transmit the information about the body condition of the user to the server 103 of the emergency center and may request a rescue.

In addition, the external device 100 may provide a notification while transmitting the information about the body condition of the user to the plurality of external apparatuses 200, 101, 102, and 103.

Although the plurality of external apparatuses 200, 101, and 102 are limited, illustrated, and described as terminal apparatuses of the user and others designated by the user for convenience of description, the plurality of external apparatuses 200, 101, and 102 may be a display apparatus such as a smart TV, a tablet PC, a PMP, a PDA, a smart watch, etc. when practically implemented.

Although the external device 100 that measures the bio signal of the user and the terminal apparatus 200 of the user are illustrated and described to be spaced apart from each other in FIG. 12 for convenience of description, the external device 100 and the terminal apparatus 200 of the user may be an all-in-one type when practically implemented. For example, if the terminal apparatus 200 of the user is a smart watch, a wrist band part of the smart watch in contact with the body of the user may be implemented to include the external device 100 that measures the bio signal of the user.

As described above, a user may frequently check information about a body condition of the user in daily life to continuously care for the user's health, and a quick rescue response may be made if an emergency occurs in the user.

The methods according to embodiments of the present disclosure may be implemented as computer instructions which may be executed by various computer means, and recorded on a non-transitory computer-readable recording medium. The non-transitory computer-readable recording medium may include program commands, data files, data structures, or a combination thereof. For example, the non-transitory computer-readable recording medium may be stored in, irrespective of whether deletion is possible or re-recoding is possible, storage devices such as volatile or non-volatile storage devices such as read only memories (ROMs), for example, memory such as random access memories (RAMs), memory chips, devices, or integrated circuits, or for example, optically or magnetically recordable and simultaneously machine (for example, computers) readable storage media. The memory that may be included in a mobile terminal may be an example of a machine readable storage medium configured to store a program or programs including instructions for implementing the embodiments of the present disclosure. The program commands recorded on the media may be for example designed for the present disclosure, constructed for the present disclosure, or may be known to and usable by one of ordinary skill in a field of computer software.

Hereinabove, although various embodiments of the present disclosure are separately described, each of the embodiments does not necessarily need to be solely implemented, but a configuration and an operation of each of the embodiments may also be implemented to be combined with one or more other embodiments.

Hereinabove, although the embodiments of the present disclosure have been shown and described, it should be understood that the present disclosure is not limited to the disclosed embodiments and may be variously changed without departing from the scope and spirit of the present disclosure. Therefore, the present disclosure is intended to be construed as including all the changes, equivalents, and substitutions included in the scope of the present disclosure as defined by the appended claims and their equivalents.

What is claimed is:

1. An electronic device, comprising:
    a communicator configured to communicate with an external device of a user by using a wireless communication; and
    a processor configured to:
    control the communicator to receive, from an external device of a user, a plurality of a first type of biometric (bio) signals of the user measured by the external device of the user,
    identify a body condition of the user, based on the plurality of the first type of bio signals of the user,
    in response to at least one of the plurality of the first type of bio signals being out of a normal range, transmit, through the communicator, a request for a second type of bio signal of the user measured by the external device of the user to the external device of the user, and
    in response to the second type of bio signal being received through the communicator from the external device of the user, additionally identify the body condition of the user by further using the second type of bio signal,
    wherein the plurality of the first type of bio signals are a different type of bio signal than the second type of bio signal, and
    wherein the processor is further configured to sense a movement of the external device of the user by using a change in a receiving direction of a signal of the wireless communication transmitted from the external device of the user and, in response to the movement of the external device of the user being not sensed for a preset time, control the communicator to request the external device of the user to transmit the plurality of the first type of bio signals of the user.

2. The electronic device as claimed in claim 1, wherein the processor is further configured to identify the body condition as one of a normal condition, a caution level, a danger condition, and an emergency condition based on the received plurality of the first type of bio signals.

3. The electronic device as claimed in claim 2, wherein the processor is further configured to transmit information about the body condition to a first external device carried by the user if the identified body condition is the caution condition, transmit the information about the body condition to at least one second external device designated by the user if the identified body condition is the danger condition, and transmit the information about the body condition to a third external device arranged in a public center if the identified body condition is the emergency condition.

4. The electronic device as claimed in claim 1, further comprising a display configured to display information about the identified body condition.

5. The electronic device as claimed in claim 2, wherein the processor is further configured to control the communicator to transmit a notification to an emergency center if the identified body condition is the emergency condition and the emergency condition continues more than a preset time.

6. The electronic device as claimed in claim 2, further comprising:
    an imaging unit configured to generate an image; and
    a microphone configured to generate voice information,
    wherein the processor is further configured to operate at least one of the imaging unit and the microphone if the identified body condition is the emergency condition and control the communicator to transmit at least one of the image generated by the imaging unit and the voice information generated by the microphone to the external device.

7. The electronic device as claimed in claim 1, wherein the processor is further configured to identify the body condition of the user in consideration of previously stored disease information of the user.

8. A method for controlling an electronic device, the method comprising:
    identifying whether a movement of an external device of a user is sensed by using a change in a receiving direction of a wireless communication signal transmitted from the external device of the user;
    in response to the movement of the external device not being sensed for a preset time, requesting the external device of the user to transmit a plurality of a first type of biometric (bio) signals of the user measured by the external device of the user;
    receiving, by a communicator, from the external device of the user, the plurality of the first type of bio signals of the user measured by the external device of the user;
    identifying, by a processor, a body condition of the user, based on the plurality of the first type of bio signals of the user;
    in response to at least one of the plurality of the first type of bio signals being out of a normal range, requesting, through the communicator, the external device of the user to transmit a second type of bio signal of the user measured by the external device of the user; and
    in response to the second type of bio signal being received through the communicator from the external device of the user, additionally identifying, by a processor, the body condition of the user further using the second type of bio signal,
    wherein the plurality of the first type of bio signals are a different type of bio signal than the second type of bio signal.

9. The method as claimed in claim 8, wherein identifying, by the processor, a body condition of the user includes identifying the body condition as one of a normal condition, a caution condition, a danger condition, and an emergency condition based on the received plurality of the first type of bio signals.

10. The method as claimed in claim 9, further comprising:
    transmitting information about the body condition to a first external device carried by the user if the identified body condition is the caution condition;
    transmitting the information about the body condition to at least one second external device designated by the user if the identified body condition is the danger condition; and transmitting the information about the body condition to a third external device arranged in a public center if the identified body condition is the emergency condition.

11. The method as claimed in claim 8, further comprising displaying information about the identified body condition.

12. The method as claimed in claim 9, further comprising transmitting a notification to an emergency center if the identified body condition is the emergency condition and an emergency level continues for more than a preset time.

13. The method as claimed in claim 9, further comprising:
   operating at least one of an imaging unit configured to generate an image and a microphone configured to generate voice information if the identified body condition is the emergency condition; and
   transmitting at least one of the image generated by the imaging unit and the voice information generated by the microphone to the external device.

14. The method as claimed in claim 8, wherein identifying, by a processor, the body condition of the user includes identifying the body condition of the user in consideration of previously stored disease information of the user.

15. A non-transitory computer-readable recording medium including a computer program for executing a method for controlling an electronic device, wherein the method includes:
   identifying whether a movement of an external device of a user is sensed by using a change in a receiving direction of a wireless communication signal transmitted from the external device of the user;
   in response to the movement of the external device not being sensed for a preset time, requesting the external device of the user to transmit a plurality of first type of biometric (bio) signals of the user measured by the external device of the user;
   receiving, by a communicator, from the external device of the user, the plurality of the first type of bio signals of the user measured by the external device of the user;
   identifying a body condition of the user based on the plurality of the first type of bio signals of the user;
   in response to at least one of the plurality of the first type of bio signals being out of a normal range, requesting, through the communicator, the external device of the user to transmit a second type of bio signal of the user measured by the external device of the user; and
   in response to the second type of bio signal being received through the communicator from the external device of the user, additionally identifying, by a processor, the body condition of the user by further using the second type of bio signal,
   wherein the plurality of the first type of bio signals are a different type of bio signal than the second type of bio signal.

* * * * *